(12) United States Patent
Kroll et al.

(10) Patent No.: US 7,899,537 B1
(45) Date of Patent: Mar. 1, 2011

(54) PERICARDIAL CARDIOVERTER DEFIBRILLATOR

(75) Inventors: Mark W. Kroll, Crystal Bay, MN (US); Yougandh Chitre, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 944 days.

(21) Appl. No.: 11/553,859

(22) Filed: Oct. 27, 2006

(51) Int. Cl.
*A61N 1/39* (2006.01)
(52) U.S. Cl. .......................... 607/36; 607/119
(58) Field of Classification Search .......... 607/4, 607/5, 9, 36
See application file for complete search history.

(56) References Cited

U.S. PATENT DOCUMENTS

| | | | |
|---|---|---|---|
| 4,073,287 A | 2/1978 | Bradley et al. | |
| 4,256,115 A | 3/1981 | Bilitch | |
| 4,693,253 A | 9/1987 | Adams | |
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,119,832 A | 6/1992 | Xavier | |
| 5,174,288 A | 12/1992 | Bardy et al. | |
| 5,249,574 A * | 10/1993 | Bush et al. | 607/9 |
| 5,411,535 A | 5/1995 | Fujii et al. | |
| 5,476,483 A | 12/1995 | Bornzin et al. | |
| 5,529,067 A | 6/1996 | Larsen et al. | |
| 5,645,586 A | 7/1997 | Meltzer | |
| 5,814,089 A | 9/1998 | Stokes et al. | |
| 5,861,024 A | 1/1999 | Rashidi | |
| 5,910,124 A * | 6/1999 | Rubin | 601/153 |
| 6,096,064 A | 8/2000 | Routh | |
| 6,141,588 A * | 10/2000 | Cox et al. | 607/9 |
| 6,208,881 B1 | 3/2001 | Champeau | |
| 6,397,109 B1 | 5/2002 | Cammilli et al. | |
| 6,643,546 B2 | 11/2003 | Mathis et al. | |
| 6,647,292 B1 * | 11/2003 | Bardy et al. | 607/5 |
| 6,907,285 B2 | 6/2005 | Denker et al. | |
| 7,274,962 B2 | 9/2007 | Bardy et al. | |
| 7,389,134 B1 | 6/2008 | Karicherla et al. | |
| 7,496,409 B2 | 2/2009 | Greenhut et al. | |
| 2002/0082647 A1 | 6/2002 | Alferness et al. | |
| 2002/0103510 A1 | 8/2002 | Bardy et al. | |
| 2002/0107549 A1 | 8/2002 | Bardy et al. | |
| 2002/0107559 A1 | 8/2002 | Sanders et al. | |
| 2003/0158584 A1 | 8/2003 | Cates et al. | |

(Continued)

FOREIGN PATENT DOCUMENTS

EP 1547648 A1 6/2005

(Continued)

OTHER PUBLICATIONS

NonFinal Office Action, mailed Mar. 17, 2009: Related U.S. Appl. No. 11/553,816.

(Continued)

*Primary Examiner*—Carl H Layno
*Assistant Examiner*—Luther G Behringer

(57) ABSTRACT

An implantable pericardial device provides therapy to a heart of a patient. In one embodiment electronics, electrodes and other components are provided in a unitary assembly. These components may be implemented such that the unitary assembly has a sufficient degree of flexibility. The implantable pericardial device may be implanted into the pericardial space using a relatively low-invasive technique such as a sub-xiphoid approach.

15 Claims, 7 Drawing Sheets

U.S. PATENT DOCUMENTS

| | | | |
|---|---|---|---|
| 2003/0199955 A1 | 10/2003 | Struble et al. | |
| 2003/0204206 A1 | 10/2003 | Padua et al. | |
| 2004/0147973 A1 | 7/2004 | Hauser | |
| 2004/0176673 A1* | 9/2004 | Wahlstrand et al. | 600/377 |
| 2004/0210292 A1 | 10/2004 | Bardy et al. | |
| 2004/0249417 A1 | 12/2004 | Ransbury et al. | |
| 2004/0249431 A1 | 12/2004 | Ransbury et al. | |
| 2005/0043765 A1 | 2/2005 | Williams et al. | |
| 2005/0149138 A1 | 7/2005 | Min et al. | |
| 2005/0192639 A1 | 9/2005 | Bardy et al. | |
| 2005/0228471 A1 | 10/2005 | Williams et al. | |
| 2009/0149902 A1* | 6/2009 | Kumar et al. | 607/4 |

FOREIGN PATENT DOCUMENTS

| | | |
|---|---|---|
| WO | WO98/26840 | 6/1998 |
| WO | WO02/49669 A2 | 6/2002 |
| WO | WO02/49669 A3 | 6/2002 |
| WO | WO02/49714 A2 | 6/2002 |
| WO | WO2005/000398 A2 | 1/2005 |
| WO | WO2005/000398 A3 | 1/2005 |
| WO | WO 2007/103262 A2 | 9/2007 |

OTHER PUBLICATIONS

Final Office Action, mailed Oct. 29, 2009: Related U.S. Appl. No. 11/553,816.

NonFinal Office Action, mailed Mar. 16, 2009: Related U.S. Appl. No. 11/553,892.

Final Office Action, mailed Oct. 30, 2009: Related U.S. Appl. No. 11/553,892.

NonFinal Office Action, mailed Jan. 22, 2010—U.S. Appl. No. 11/553,816.

NonFinal Office Action, mailed Jan. 15, 2010—Related U.S. Appl. No. 11/553,842.

* cited by examiner

PERICARDIAL CARDIOVERTER DEFIBRILLATOR

CROSS-REFERENCE TO RELATED APPLICATIONS

This application is related to U.S. patent application Ser. No. 11/553,816, filed concurrently herewith, titled "CONFIGURABLE IMPLANTABLE MEDICAL DEVICE"; and U.S. patent application Ser. No. 11/553,842, filed concurrently herewith, titled "IMPLANTABLE MEDICAL DEVICE".

TECHNICAL FIELD

This application relates generally to implantable cardiac devices and, in some embodiments, to a cardioverter defibrillator apparatus that is implantable in the pericardial space.

BACKGROUND

Implantable cardiac devices are used to treat a patient's heart that does not function normally due to, for example, a genetic or acquired condition. A typical implantable cardiac device may perform one or more functions including sensing signals generated in the heart, pacing the heart to maintain regular contractions and providing defibrillation shocks to the heart. Various techniques have been used to implant a cardiac device and associated leads.

An endocardial implantation technique generally involves gaining access to the interior of the heart via the venous return and implanting several leads within the heart. For example, an implantable device including circuitry for sensing signals from and generating stimulation signals for the heart may be subcutaneously implanted in the pectoral region of the patient. Leads connected to the device are routed from the device through a vein to the right side of the heart. A distal end of the lead may then be passively or actively attached to an inner wall of the heart.

An epicardial implantation technique generally involves implanting leads at an outer layer of the heart (the epicardium). Historically, an implantable device including the sensing and pacing circuitry was implanted in the abdominal region of the patient. Sensing/stimulation leads were then run from the device to the epicardium.

Alternatively, the device also may be implanted in the pectoral region of the patient for an epicardial implantation technique. In this case, a tunnel is formed under the patient's skin between the implant site for the device and the heart. Leads are then routed via the tunnel from the device to the lead implant site in the epicardium.

There are several disadvantages that may be associated with the above implantation techniques. For example, placement of the implanted device in the abdomen may be relatively uncomfortable for the patient. In addition, defibrillation vectors that incorporate the implanted device as an electrode may be suboptimal. Conversely, creating a tunnel between the pectoral region and the heart may be traumatic for a patient and may require a relatively long recovery period.

SUMMARY

A summary of selected aspects and/or embodiments of an apparatus constructed or a method practiced according to the invention follows. For convenience, an embodiment of an apparatus constructed or a method practiced according to the invention may be referred to herein simply as an "embodiment."

In some aspects the invention relates to a cardiac device that is implantable in the pericardial space. In some embodiments the device may provide the functionality of a cardioverter defibrillator. Hence, for convenience, the device may be referred to herein as a pericardial ICD (implantable cardioverter defibrillator). Cardiac device components such as electronics, capacitors and a battery may be integrated with cardiac lead components such as a lead body and electrodes to provide a unitary assembly. These components may be implemented such that the unitary assembly is sufficiently flexible to facilitate implanting the unitary assembly in the pericardial space. The pericardial ICD may thus provide therapy to the heart without the need for any physical connection to any external components. As a result, some of the disadvantages that may be associated with other cardiac device implantation methods (e.g., undesirable placement of a cardiac device or tunneling to route leads from a cardiac device to the heart) may be avoided.

In some embodiments the components of the pericardial ICD are implemented in a manner that facilitates providing a device with appropriate flexibility. For example, the electronic components, the capacitors and the battery may be physically separated. In addition, flexible mechanical and electrical interconnections may be provided between these components to achieve the desired overall flexibility of the device. These interconnections may be sized (e.g., of a sufficient length) to enable the device to bend as necessary to conform to the contour of the surface of the epicardium.

In some embodiments the pericardial ICD incorporates a flexible, hermetically sealed housing for the electronic components, the capacitors, the battery and other components. The flexible housing may include a conductive outer layer to facilitate using the housing as an electrode. Accordingly, in some embodiments at least a portion of the flexible housing is made from a conductive material such as a conductive polymer.

In some embodiments the pericardial ICD may be implanted using a relatively non-invasive technique. For example, a sub-xiphoid approach may be used to insert the device into the patient. In this way, relatively safe and easy access may be gained to the pericardial space. Accordingly, a cardiac device may be implanted in a patient without accessing the vascular system. Implantation may thereby be achieved without significant surgical intervention or the use of general anesthesia.

Advantageously, access may be gained to the entire exterior of the heart (e.g., any chamber, blood vessel or other anatomical feature of the heart) by implanting the device though a single entry point in the pericardial sac. Thus, the electrodes of the pericardial ICD may be configured to provide various forms of therapy. For example, multiple electrodes may be provided of sufficient sizes and spacing to provide therapy to multiple chambers of the heart. In addition, electrodes may be positioned along the device and the device implanted such that the electrodes are located diametrically across from one another after implantation. As a result, the device may be configured to provide very effective sensing, stimulation therapy or shocking therapy.

BRIEF DESCRIPTION OF THE DRAWINGS

These and other features, aspects and advantages of the invention will be more fully understood when considered with respect to the following detailed description, appended claims and accompanying drawings, wherein:

Figure 1:
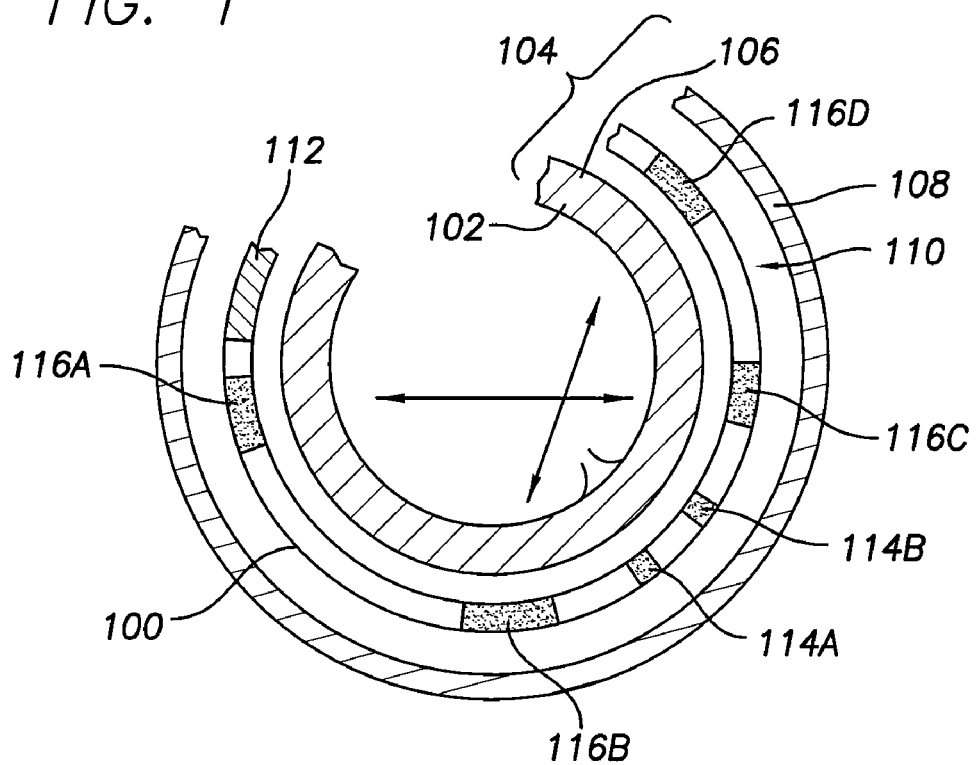
FIG. 1 is a simplified diagram of one embodiment of a pericardial ICD implanted in a pericardial space of a patient's heart for sensing signals in the heart and delivering pacing and shock therapy.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

Aspects of the invention are described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s). Accordingly, references to "an" or "one" embodiment in this discussion are not necessarily to the same embodiment, and such references mean at least one embodiment.

In some aspects, the invention relates to implanting a device into a pericardial space of a heart. Referring to the partial cutout view of a heart in FIG. 1, a human heart includes myocardium muscle tissue 102 that is contained within a pericardial sac 104. The myocardium 102 consists of specialized cardiac muscle cells that contract in response to electrical signals in the heart. The outer layer of myocardial heart tissue is referred to as the epicardium 106.

The pericardium 104 serves to contain and protect the heart. An outer layer 108 of the pericardium is anchored to surrounding walls of the body (not shown). A small space 110 containing pericardial fluid exists between the outer pericardial layer 108 and the epicardium 106. The combination of the outer pericardial layer 108, the epicardium 106 and the lubricating fluid in the pericardial space 110 serves to reduce friction that would otherwise occur between the beating heart and surrounding tissue. Conventionally, the epicardium 106 may be considered as part of the pericardium 104. For convenience of discussion, however, references to the pericardium 104 herein generally will refer to pericardial layers outside of the epicardium 106.

In FIG. 1 a pericardial ICD device 100 is shown implanted in the pericardial space 110. For clarity, both the device 100 and the pericardial space 110 are depicted enlarged relative to the other components of the heart. The device 100 includes, in a unitary assembly, cardiac device components 112 such as electronics, a capacitor and a battery and cardiac lead components such as electrodes. The device 100 is fabricated in such a manner as to enable the device to conform to the shape of the pericardial space (e.g., conform to the shape of the surface of the epicardium) to reduce trauma in that area.

In general, some of the functionality of the cardiac device components 112 is similar to functionality that has conventionally been implemented in a separate implantable cardiac device (e.g., implanted subcutaneously in a patient's pectoral region). For example, the electronics may include a processor, switches, sensing circuits and pulse generating circuits to sense conditions in the heart and generate appropriate stimulation signals that are applied to the heart.

The functions of some of the cardiac lead components are similar to functions that traditionally would have been implemented in a separate lead that connects to an implantable cardiac device on one end and is implanted in the heart on the other end. For example, the device 100 includes electrodes for sensing signals in the heart and delivering stimulation signals to the heart. In the example of FIG. 1, two electrodes 114A, 114B are used for sensing and pacing and four electrodes 116A, 116B, 116C and 116D are used for delivering defibrillation shocks. It should be appreciated that the specific electrodes shown in FIG. 1 are merely illustrative of one configuration of a pericardial ICD and that a given pericardial ICD may incorporate a different number and different types of electrodes.

The electrodes may be spaced along the device 100 to facilitate positioning the electrodes at desired locations in the pericardial space. For example, when the device 100 is implanted different electrodes in the device 100 may be positioned adjacent different chambers of the heart.

In addition, the electrodes may be spaced and positioned to provide a desired sensing or stimulation vector. For example, as illustrated in FIG. 1 one or more pairs of electrodes may be positioned diametrically opposite (or substantially diametrically opposite) one another across the heart (as represented by each arrow). As a result of advantageous electrode placements (e.g., that provide orthogonal or substantially orthogonal vectors) that may be achieved using the device 100; the resulting shock mechanism may be extremely efficient. For example, shocking therapy may be accomplished with a relatively low defibrillation threshold.

Figure 2:
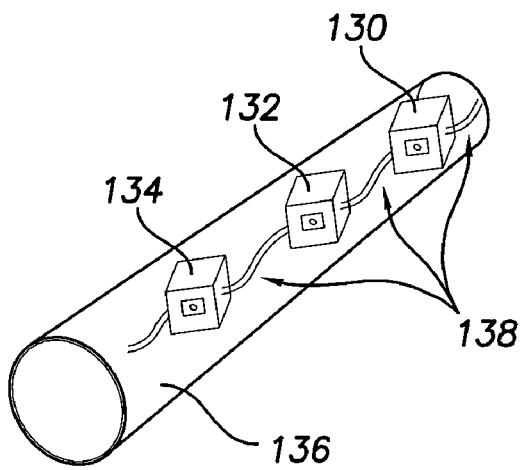
FIG. 2 is a simplified diagram of one embodiment of a housing for cardiac device components of a pericardial ICD.

To improve the overall flexibility of the device 100, the cardiac device components 112 may be implemented in a housing made of a flexible material that has a suitable durometer so as to accommodate conformance to the epicardial surface. For example, as illustrated in FIG. 2 several components 130, 132 and 134 (e.g., components 112 discussed above) are provided in a housing 136 composed of a flexible polymer. In some embodiments at least an external portion of the housing may be electrically conductive to provide an electrode associated with the cardiac device components 112. Such an electrode may provide a function similar to a traditional "can" electrode or function as shocking electrode or some other form of electrode. A conductive polymer may comprise, without limitation, silicone, a polyurethane-based polymer or a co-polymer (e.g., a combination of the two) that is impregnated with a conductive material such as platinum, indium, gold, silver, etc.

To further improve the overall flexibility of the device 100, the cardiac device components 112 may be physically separated from one another. For example, as illustrated in FIG. 2 microelectronic components 130, a capacitor component 132 and a battery component 134 may be positioned substantially along a longitudinal axis of the device 100. The housing 136 or some other mechanism (e.g., a flexible fixation member, not shown) may be used to mechanically interconnect the components. In addition, an electrical interconnection (e.g., one or more electrical conductors) 138 may be used to provide power and/or signal connections between the components 130, 132 and 134. It should be appreciated that the above examples of interconnections are merely illustrative and that other forms of mechanical interconnections may be used to hold the components relative to one another or to the housing, and that other forms of electrical interconnections (e.g., one using another signal medium) may be used to enable signals and/or power to pass from one component to another.

A given cardiac device component may be divided into multiple components to further improve the overall flexibility of the device 100. Here, each individual sub-component may be made smaller than the unitary component, thereby reducing the resistance to bending that may be present if larger (e.g., longer and wider) unitary components were used. For example, the functionality of the electronic component 130 may be performed by several electronic subcomponents that are physically separated and interconnected (e.g., as discussed above). These subcomponents also are adapted to cooperate, as necessary, with the other sub-components or other components in the device 100. Similarly, the functionality of the capacitor component 132 and/or the battery component 134 may be provided by several smaller capacitors and/or batteries that are physically separated and interconnected (e.g., as discussed above). In one embodiment the device 100 includes two capacitors to provide the desired charge storage.

It should be appreciated that the device 100 may include components other than those specifically shown. For example, the device may include other types of electrodes, sensors or devices that serve to otherwise interact with a patient or the surroundings. For example, in some embodiments the device 100 includes one or more physiologic sensors.

Figure 3:
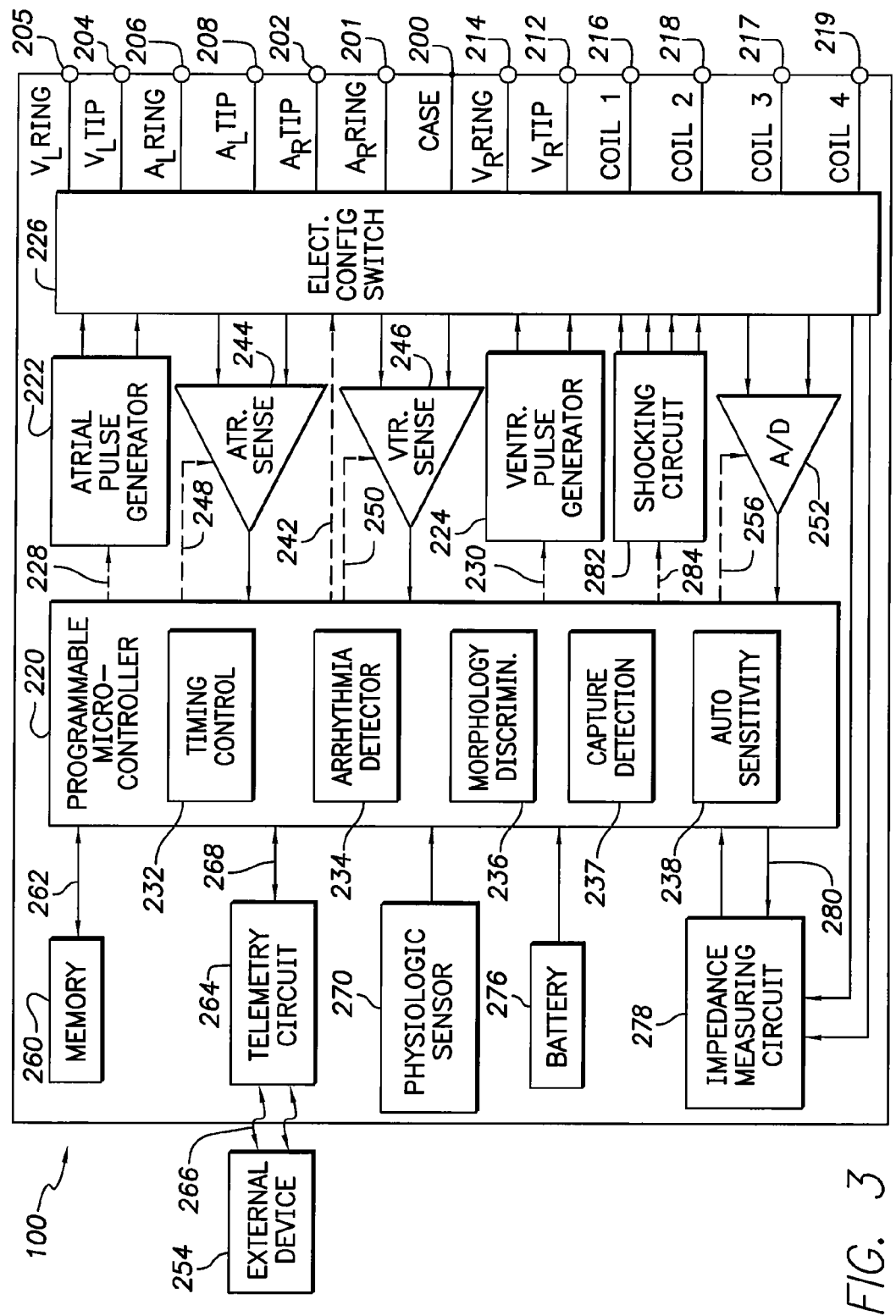
FIG. 3 is a simplified functional block diagram of one embodiment of cardiac device components in a pericardial ICD constructed in accordance with the invention, illustrating basic elements that are configured to provide cardioversion, defibrillation or pacing stimulation or any combination thereof.

Referring to FIG. 3, exemplary cardiac device components (e.g., components 112 discussed above) that may be incorporated in a pericardial ICD device 100 will now be described in more detail. It is to be appreciated and understood that other cardiac device components may be used and that the description below is given, in its specific context, to assist the reader in understanding, with more clarity, the embodiments described herein.

The device 100 may be configured to treat both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable device. Accordingly, one of skill in the art could readily duplicate, eliminate, or disable the appropriate circuitry in any desired combination to provide a pericardial ICD capable of treating the appropriate chamber(s) with, for example, one or more of cardioversion, defibrillation, or pacing stimulation.

As discussed above, a conductive housing 200 for the cardiac device components may be referred to as the "can", "case" or "case electrode." The conductive housing 200 may be programmably selected to act as the return electrode for all "unipolar" modes. Housing 200 may further be used as a return electrode alone or in combination with one or more of the electrodes 116A-D (e.g., coil electrodes) for shocking purposes. The device 100 further includes one or more interconnection mechanisms to connect the cardiac device components to the electrodes or other components in the device 100. For example, the device 100 may include a connector (not shown) having a plurality of terminals 201, 202, 204, 205, 206, 208, 212, 214, 216, 217, 218 and 219. The terminals are shown schematically and, for convenience, the names of the electrodes to which they may be connected are shown next to the terminals. The connector may be configured to include various other terminals depending on the requirements of the device.

To achieve right atrial sensing and pacing, the connector includes, for example, a right atrial tip terminal (A$_R$ TIP) 202 adapted for connection to a right atrial tip electrode or similar electrode in the device 100. A right atrial ring terminal (A$_R$ RING) 201 also may be included and adapted for connection to a right atrial ring electrode or similar electrode in the device 100.

To achieve left atrial sensing and pacing, the connector includes, for example, a left atrial tip terminal (A$_L$ TIP) 208 adapted for connection to a left atrial tip electrode or similar electrode in the device 100. A left atrial ring terminal (A$_L$ RING) 206 also may be included and adapted for connection to a left atrial ring electrode or similar electrode in the device 100.

To achieve left ventricle sensing and pacing, the connector includes, for example, a left ventricular tip terminal (V$_L$ TIP) 204 adapted for connection to a left ventricular tip electrode (e.g., electrode 114A) or similar electrode in the device 100. A left ventricular ring terminal (V$_L$ RING) 205 also may be included and adapted for connection to a left ventricular ring electrode (e.g., electrode 114B) or similar electrode in the device 100.

To achieve right ventricle sensing and pacing, the connector includes, for example, a right ventricular tip terminal (V$_R$ TIP) 212 adapted for connection to a right ventricular tip electrode or similar electrode in the device 100. A right ventricular ring terminal (V$_R$ RING) 214 also may be included and adapted for connection to a right ventricular ring electrode or similar electrode in the device 100.

To achieve shocking, the connector includes, for example, terminal 216 (COIL 1), terminal 217 (COIL 3), terminal 218 (COIL 2) and terminal 219 (COIL 4) adapted for connection to electrodes 116A, B, D and D, respectively, or similar electrodes in the device 100.

At the core of the device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by atrial electrode(s) and ventricular electrode(s), respectively, via an electrode configuration switch 226. It is understood that in order to provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 may be utilized by the device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 may include a morphology discrimination module 236, a capture detection module 237 and an auto sensing module 238. These modules are optionally used to implement various exemplary recognition algorithms and/or methods. The aforementioned components may be implemented in hardware as part of the microcontroller 220, or as software/firmware instructions programmed into the device and executed on the microcontroller 220 during certain modes of operation.

The electrode configuration switch 226 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 226, in response to a control signal 242 from the microcontroller 220, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 244 and ventricular sensing circuits (VTR. SENSE) 246 may also be selectively coupled to one or more atrium-related electrodes and one or more ventricle-related electrodes, respectively, through the switch 226 for detecting the presence of cardiac activity in each of the four chambers of the heart. Accordingly, the atrial and ventricular sensing circuits 244 and 246 may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., circuits 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252. This information may be used to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits 244 and 246 as is known in the art.

For arrhythmia detection, the device 100 utilizes the atrial and ventricular sensing circuits 244 and 246 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 252. The data acquisition system 252 is configured (e.g., via signal line 256) to acquire intracardiac electrogram ("IEGM") signals or other signals, convert the raw analog data into a digital signal, and store the digital signals for later processing and/or telemetric transmission to an external device 254. The data acquisition system 252 is coupled to the atrial electrode(s), the ventricular electrode(s) and other electrodes through the switch 226 to sample cardiac signals across any pair of desired electrodes.

The data acquisition system 252 also may be coupled to receive signals from other input devices. For example, the data acquisition system 252 may sample signals from a physiologic sensor or other components shown in FIG. 2 (connections not shown).

The microcontroller 220 is further coupled to a memory 260 by a suitable data/address bus 262, wherein the programmable operating parameters used by the microcontroller 220 are stored and modified, as required, in order to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The device 100 can further include or connect to one or more physiologic sensors. In some embodiments the device may include a "rate-responsive" sensor that may provide, for example, information to aid in adjustment of pacing stimulation rate according to the exercise state of the patient. One or more physiologic sensors (e.g., a pressure sensor) may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators 222 and 224 generate stimulation pulses.

While shown as being included within the device 100, it is to be understood that a physiologic sensor may be external to the device 100, yet still be implanted within or carried by the patient. Examples of physiologic sensors that may be implemented in conjunction with device 100 include sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors may optionally include sensors to help detect movement (via, e.g., a position sensor) and/or minute ventilation (via an MV sensor) in the patient. Signals generated by the position sensor and MV sensor may be passed to the microcontroller 220 for analysis in determining whether to adjust the pacing rate, etc. The microcontroller 220 may thus monitor the signals for indications of the patient's position and activity status, such as whether the patient is climbing up stairs or descending down stairs or whether the patient is sitting up after lying down.

The device additionally includes a battery 276 (e.g., battery component 134 discussed above) that provides operating power to all of the circuits shown in FIG. 2. For a device 100, which employs shocking therapy, the battery 276 is capable of operating at low current drains (e.g., preferably less than 10 μA) for long periods of time, and is capable of providing high-current pulses (for charging one or more capacitors, e.g., capacitor component 132 discussed above) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or similar battery technology.

The device 100 can further include magnet detection circuitry (not shown), coupled to the microcontroller 220, to detect when a magnet is placed over the device 100. A magnet may be used by a clinician to perform various test functions of the device 100 and/or to signal the microcontroller 220 that the external device 254 is in place to receive data from or transmit data to the microcontroller 220 through the telemetry circuits 264.

The device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart through, for example, two shocking electrodes. As noted above, the housing 200 may act as an active electrode in combination with a shocking electrode, and/or as part of a split electrical vector with a shocking electrode.

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

With the above description in mind, one embodiment of an implantation method for a pericardial ICD will now be described in conjunction with FIG. 4. As represented by block 402, in some embodiments the pericardium is accessed using a relatively minimally-invasive procedure. Such a procedure may involve an intercostal, sub-xiphoid or other access technique. For example, referring to FIG. 5, a pericardial ICD device 100 may be inserted into a mid-chest region 502 of a patient P. As illustrated by the cut-out region 504 in FIG. 5, the device 100 is routed through the body of the patient to the pericardium 506 of the heart H of the patient P. Advantageously, an intercostal, sub-xiphoid or similar procedure may be significantly simpler and faster and may require a shorter postoperative recovery period than surgical techniques used with the endocardial or epicardial procedures discussed above.

Various imaging techniques may be used during the implantation procedure. In some embodiments, the instruments used during implant and/or the device 100 may include markers that enable the physician to observe the location of the instruments using, for example, fluoroscopy. Alternatively, imaging techniques such as MRI, endoscopy, X-ray, ultrasound, etc., may be used to track the location of an instrument or the device 100 within the patient.

Figure 5:
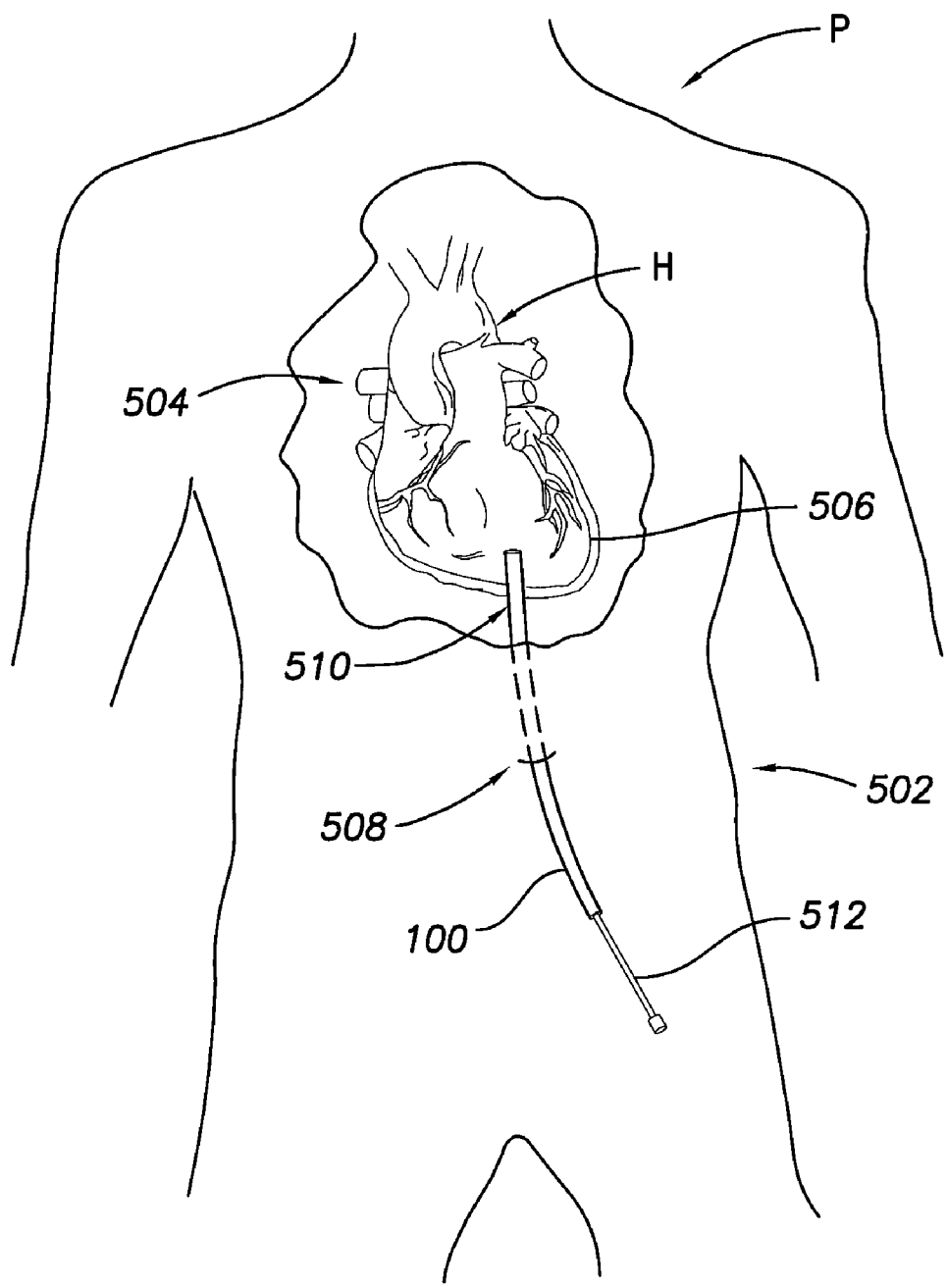
FIG. 5 is a simplified diagram of one embodiment of a sub-xiphoid access technique.

One or more incisions 508 for receiving various instruments are made in the mid-chest region 502. In a sub-xiphoid technique, an incision 508 is made in an area below the sternum. Although FIG. 5 illustrates one incision, two or more incisions may also be employed. In addition, the location and size of each incision and the types of instruments used may vary depending upon the patient's anatomy and the preferences of the physician and/or the electro-physiologist. Each incision may accommodate a trocar (not shown) for facilitating the insertion and manipulation of one of the instruments.

Figure 4:
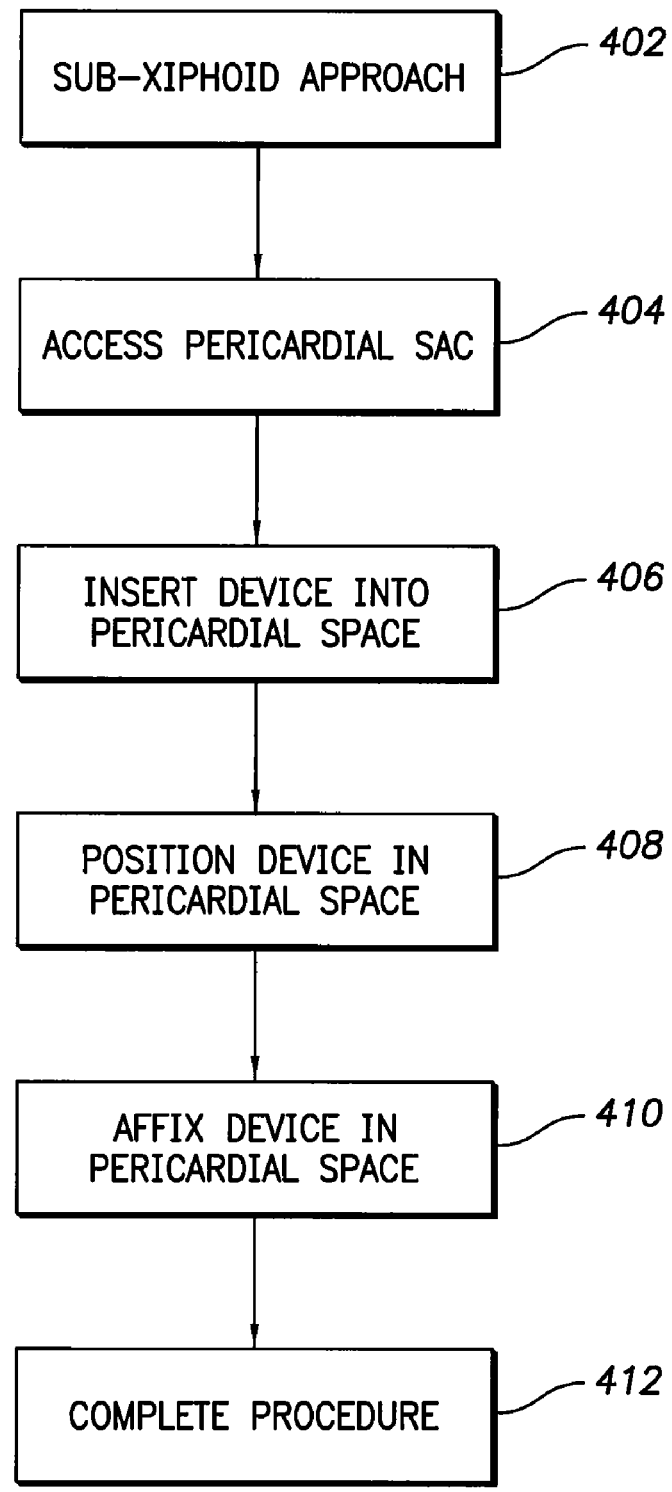
FIG. 4 is a simplified flow chart of one embodiment of operations that may be performed to implant a pericardial ICD.

As represented by block 404 in FIG. 4, once the initial incision is made in the patient, an instrument (not shown) is used to pierce the outer layer of the pericardium 506 to provide an access hole 510. In some embodiments a guide wire 512 is then routed through a lumen in the piercing instrument such that the guide wire 512 passes through the incision and the access hole 510 then into the pericardial space. Once the guide wire 512 is in place, the piercing instrument may be withdrawn.

As represented by block 406, the device 100 may be routed over the guide wire into the pericardial space. Referring to the partial cutout view of FIG. 6, the device 100 is thus fed between the pericardium 602 and the epicardium 604.

In some embodiments the guide wire 512 or some other mechanism is used to direct the device 100 along a desired path. In this way, the electrodes on the device 100 may be placed at desired positions in the pericardial space (block 408). For example, as discussed above, the electrodes may be positioned to provide sensing/stimulation in one or more chambers of the heart. Accordingly, the device 100 may be routed to position one or more electrodes adjacent the desired chambers. In addition, as depicted in FIG. 1 for example, electrode pairs may be placed in certain positions relative to one another.

Figure 6:
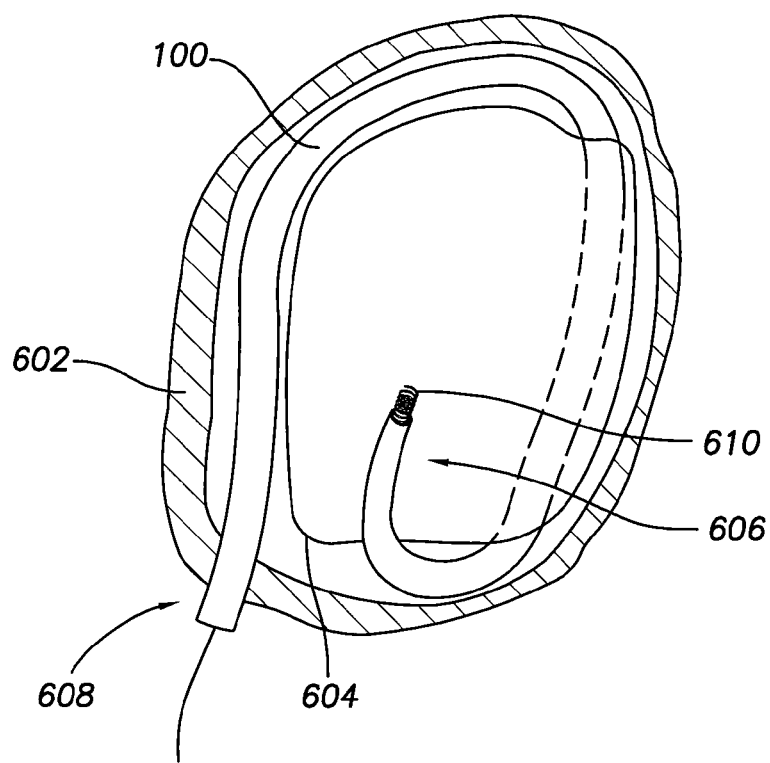
FIG. 6 is a simplified diagram illustrating one embodiment of a technique for implanting a pericardial ICD in a pericardial space.
Figure 7:
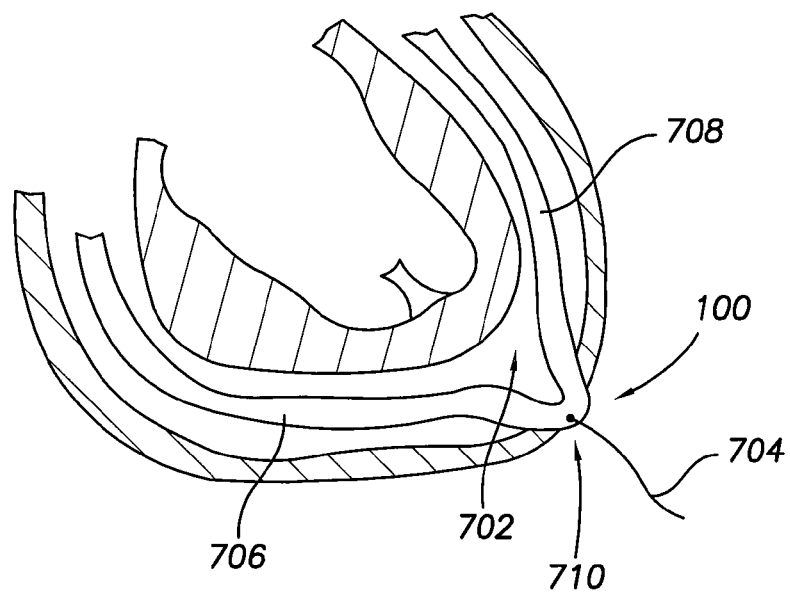
FIG. 7 is a simplified diagram illustrating one embodiment of a technique for implanting a pericardial ICD in a pericardial space.

FIG. 6 illustrates an embodiment where a device 100 may be implanted in the pericardial space by first inserting a distal end 606 of the device 100 then pushing the device 100 into the pericardial space until a proximal end 608 of the device is pushed into the pericardial space. It should be appreciated, however, that other techniques may be used to implant the device 100. For example, FIG. 7 illustrates an embodiment where each end of a device 100 is inserted into the pericardial space 702. For example, one or more guide wires or other mechanisms 704 may be used to steer a first portion 706 of the device 100 along a first path and to steer a second portion 708 of the device 100 along a second path. Here, one of the portions may be implanted before the other portion, or the portions may be implanted concurrently. The device 100 may include one or more access holes 710 for the guide wire(s) or mechanism(s) 704. Here, provisions may be made to seal an access hole 710 after implant or provisions may be made ensure that an access hole 710 does not compromise the functionality or the reliability of the device 100.

In some embodiments, the device 100 may be initially inserted into the pericardial space by a mechanism other than a guide wire. In this case, after the device is initially implanted a positioning mechanism such as a guide wire may be used to move the device 100 to a desired location.

As represented by block 410, once the device 100 is implanted at a desired position, the device may be fixed in place. For example, the device 100 may include one or more active fixation mechanisms (e.g., helix 610 on a distal end of the device 100 in FIG. 6) or one or more passive fixation mechanisms such as tines (not shown). It should be appreciated that a variety of mechanisms may be employed to fix the device 100 in the pericardial space. For example, the device 100 may be adhered using an adhesive that is, for example, injected into the pericardial space via a lumen in the device 100. In addition, the device 100 may include hooks or barbs that "catch on" adjacent heart tissue. Typically, a fixation mechanism is directed toward the epicardial surface to hold the device 100 (and, hence, one or more of the electrodes) against the epicardium. The device 100 may be at least partially held in place by wrapping the device 100 around the heart (e.g., as shown in FIG. 6). The device 100 also may be wedged in place. For example, a portion of the device 100 or a member protracting from the device 100 may be forced into folds in the surface of the epicardium.

As represented by block 412, once the device 100 is fixed in place, any instruments used during the implant procedure may be removed and the patient closed up as necessary. The device 100 may then be initialized and tested prior to commencing full operation. In some embodiments, more than one device 100 may be implanted in the patient. The above operations may thus be repeated for each additional device 100.

Figure 8:
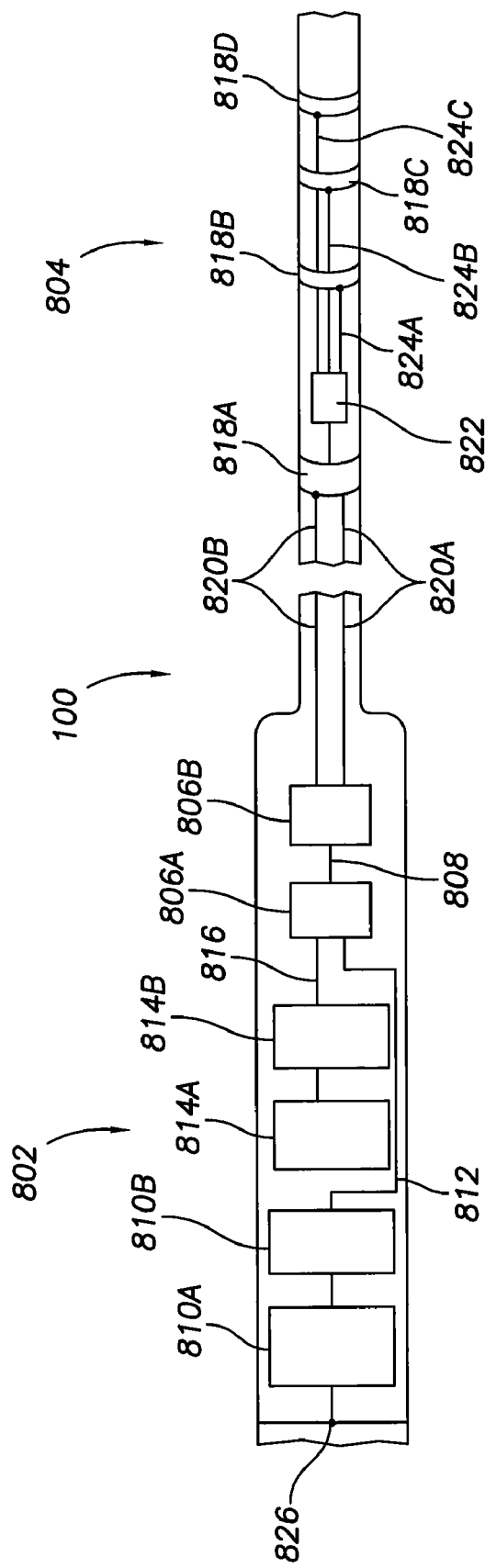
FIG. 8 is a simplified diagram of one embodiment of a pericardial ICD.

A pericardial ICD device may configured with an appropriate size and shape to provide desired functionality and performance. FIG. 8 illustrates in a more detail one embodiment of a pericardial ICD device 100 where the cross section(s) and the length of the device 100 are selected to accommodate the circuitry necessary for providing the desired functionality and a desired level of performance. For example, one or more portions 802 of the device 100 may have a larger cross section than other portions 804 of the device 100. This configuration may be used, for example, to accommodate larger components in a wider portion 802. In some embodiments a smaller cross section portion has a cross section (e.g., diameter) on the order of 3 mm and a larger cross section portion has a cross section (e.g., diameter) on the order of 9 mm.

In some embodiments the portions may have a relatively circular cross section (e.g., as illustrated in FIG. 2). Such a configuration may facilitate routing the device 100 through the various twists and turns that may be encountered as the device 100 is implanted. It should be appreciated, however, that the device 100 may be constructed with other cross section configurations.

In a typical embodiment, a wider portion 802 may be located on one end or both ends of the device 100. For example, in the embodiment of FIG. 6, the microelectronics, capacitors and battery may be located on the distal end 606 or the proximal end 608 of the device 100. It should be appreciated, however, that a wider portion may be incorporated into other areas of the device 100.

The device 100 also may be constructed with a length that is sufficient to accommodate all of the necessary circuitry. The use of physically separated components as described herein may necessitate that the device 100 be sufficiently long to accommodate the components while maintaining sufficient flexibility of the device 100. In some embodiments the device 100 may have length on the order of 55-100 cm. It should be appreciated that other lengths may be used depending on the requirements of a given application. In instances where the length of the device 100 is relatively long, the device 100 may be wrapped around the heart to accommodate any excess length (e.g., as shown in FIG. 6).

FIG. 8 illustrates an embodiment where functionality for a given component is provided by various subcomponents. The device 100 includes several microelectronics subcomponents 806A, B that communicate with one another via an electrical interconnection 808. The electrical interconnection 808 may implement, for example, parallel or serial bus architecture or some other communication architecture. Typically, the connections are made using flexible conductors. It should be appreciated, however, that another form of medium may be used to provide inter-subcomponent communications. In addition, several battery subcomponents 810A, B may provide a desired amount of storage capacity in a structure having a sufficiently small cross section. The battery subcomponents 810A, B may be interconnected and connect with the microelectronic subcomponents 806A, B via an appropriate electrical interconnection (e.g., a pair of electrical conductors) 812. Several capacitor subcomponents 814A, B may provide a desired amount of charge storage capacity in a structure having a sufficiently small cross section. The capacitor subcomponents 814A, B may be interconnected and connect with the microelectronic subcomponents 806A, B and, in some embodiments, the battery subcomponents 810A, B via an appropriate electrical interconnection (e.g., a pair of electrical conductors) 816.

FIG. 8 also shows in a simplified form one embodiment of interconnections between the microelectronics 806A, B and electrodes (e.g., electrodes 818A-D) in the device 100. Here, one or more conductors (e.g., conductors 820A, B) are routed from the microelectronics 806A, B through the device 100 to the electrodes 818A-D. As in conventional cardiac leads, a conductor may be a coil routed adjacent an exterior surface of the device 100 or insulated conductors routed through lumens within the device 100.

In some embodiments an interconnection may incorporate one or more multiplexers 822. For example, a multiplexer 822 maybe used to multiplex signals carried over multiple signal leads 824A-C that are connected to different electrodes 818B-D to/from a signal lead 820A that is connected to the microelectronics 806A, B. In some embodiments, a multiplexer 822 may be used to select one electrode of a group of electrodes to be used for a given sense/stimulation operation. For example, as shown in FIG. 8 one of three electrodes 818B-D may be associated with more desirable signal characteristics. Here, tests may be performed with each electrode to identify the electrode with the most desirable associated signal characteristics. The multiplexer 822 may then be configured to connect the selected electrode to the microelectronics 806A, B via the lead 820A to provide sensing/stimulation, for example, in conjunction with some other electrode (e.g., electrode 818A).

The electrodes in a pericardial ICD device may be implemented using a conductive material such as a conductive polymer, metal (e.g., platinum) or any other conventional electrode material. In some embodiments an electrode may include a coating of titanium nitride to improve the sensing characteristics of the electrode.

An electrode may be sized and spaced relative to the device 100 based in the intended function of the electrode. Several examples follow. An electrode configured to function as a tip electrode (e.g., an anode) may have a surface area on the order of 2-10 $mm^2$. An electrode configured to function as a ring electrode (e.g., a cathode) may have a surface area on the order of 14-35 $mm^2$. For bi-polar operation, the spacing between the electrodes (e.g., similar to "tip" and "ring" electrodes) may be on the order of 1-15 mm. For shock electrodes, a cross section (e.g., diameter) on the order of 4-12 French may be used along with a length on the order of 3-5 cm.

As discussed above, the body (e.g., housing) of the device 100 is constructed of a material having sufficient flexibility to accommodate the shape of the pericardial space. For example, the body may be constructed of silicone, a polyurethane-based polymer or a co-polymer (e.g., a combination of the two). In some embodiments one or more of the components may be encapsulated in the body of the device (e.g., embedded in a polymer).

In some embodiments the device 100 is formed as a continuous structure (e.g., an elongated polymer-based member) having conductive sections (for each electrode). Here, the entire member may thus serve as a housing for the microelectronics component, the capacitor component, the battery component, the electrodes and the interconnections.

Alternatively, the device 100 may be constructed by combining different subsections and providing appropriate interconnection and mechanical coupling and/or bonding. For example, one flexible housing may be provided for one or more of a battery component, a microelectronics component, a capacitor component or interconnections. Another flexible housing may then be provided for the electrodes and interconnections.

In some embodiments provisions may be made to enable a component of the device 100 to be replaced. For example, a portion of the device 100 (e.g., a housing including one or more of a battery component, a microelectronics component, a capacitor component or interconnections) may be detachable from another portion of the device. To this end, the respective portions may include releasable electrical, and optionally mechanical, connectors. In addition, provisions may be made at the common boundary of the portions to ensure that an appropriate seal is made at the boundary, as necessary, when the replacement portion is mated with the portion that remained implanted. By providing replaceable portions, components such as batteries that need to be replaced or microelectronics or capacitors that are to be upgraded may be replaced without replacing the entire device (e.g., electrodes that are securely fixed in the pericardial space).

In some embodiments the device 100 includes a mechanism to recharge the battery component 810A, B. For example, the device 100 may include a connector 826 to which an external lead (not shown) may connect to provide recharging power to the battery. In such an embodiment, either the external lead may be routed into the body to the implant location of the connector 826, or the device 100 (e.g., portion 802) may be partially removed so that the connector 826 is made accessible outside of the pericardial space.

The device may include one or more lumens (not shown). For example, a fluid lumen may be provided to deliver a drug to a selected site (e.g., at an active fixation site) and/or to deliver an adhesive, for example, during implant. In addition, as discussed above one or more lumens in the device may accommodate electrical conductors that are routed between various components (e.g., electrodes, sensors, etc.) in the device 100.

Figure 9:
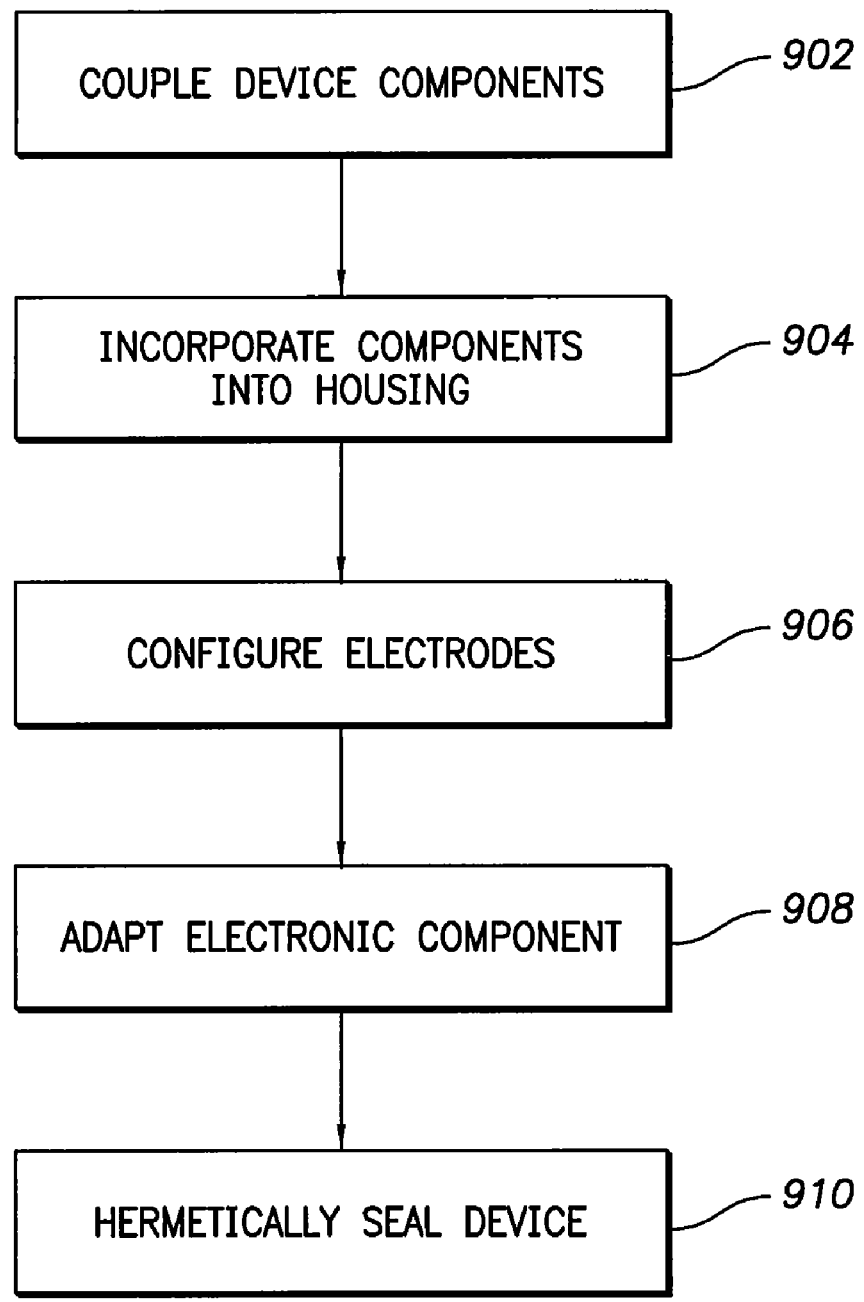
FIG. 9 is a simplified flow chart of one embodiment of operations that may be performed to provide a pericardial ICD.

In some aspects the invention relates to a method of making an implantable pericardial device (e.g., ICD). FIG. 9 illustrates one embodiment of such a method. As represented by block 902, an electronic component is coupled to several electrodes, a capacitor component and a battery component. As discussed above, these components may comprise several subcomponents. The coupling may be accomplished through the use of one or more interconnections. Typically, these interconnections comprise flexible conductors and, optionally, associated connectors.

As represented by block 904, at least one housing is provided for the electronic component, the electrodes, the capacitor component, the battery component and the interconnections. In some embodiments all of these components are incorporated into a unitary structure.

Alternatively, a portion of the components may be incorporated into one housing while another portion of the components are incorporated into another housing. These individual housings may be combined to provide an integrated housing. In this case, the coupling of some of the components described at block 902 may be performed after some of the components are incorporated into a housing.

A variety of techniques may be used to incorporate components into a housing. For example, in some embodiments the components may be encapsulated into the housing material (e.g., a polymer). In other embodiments, the components may be inserted into an interior space of a housing. In this case appropriate mechanical fastening mechanisms may be employed to maintain the position of a component relative to the housing and/or other components.

As represented by block 906, as the electrodes are incorporated into the device 100 (e.g., into the housing), the electrodes may be configured to provide the desired sensing and/or stimulation vectors. For example, as discussed above the electrodes may be sized and spaced in a manner that provides a bipolar (e.g., similar to a tip-ring) electrode. In addition, the electrodes may be located on the device 100 to enable the electrodes to be positioned upon implant adjacent a given chamber or other area of the heart. Also, the electrodes may be sized and located such that desired vectors (e.g., orthogonal vectors) may be achieved upon implant.

In some embodiments a component such as an electrode may be provided in conjunction with the manufacture of a housing. For example, an electrode may be formed in a housing by impregnating a portion of the housing with a conductive material and/or by attaching a conductor to the housing. Again, the coupling of some of the components described at block 902 may thus be performed as or after some of the components are incorporated into a housing.

As represented by block 908, the electronic component may be adapted to sense cardiac signals, generate cardiac stimulation signals (e.g., pacing signals or defibrillation shock signals) or perform other operations. This may involve, for example, assembling the appropriate components and, if applicable, programming a programmable device. All or a portion of the programming or other configuration operations may be performed before or after the electronic component is incorporated into the housing.

As represented by block 910, the device may be hermetically sealed. For example, the device may be sealed in its entirety or local sealing may be provided in and around critical components. As an example of the latter case, the battery component, the microelectronics component and the capacitor component may be individually hermetically sealed with appropriate interconnections protruding from each sealed component.

It should be appreciated from the above that the various structures and functions described herein may be incorporated into a variety of apparatuses and implemented in a variety of ways. For example, different embodiments may include different structural components and different hardware and software processing components. In some embodiments, hardware components such as processors, controllers, state machines and/or logic may be used to implement the described components or circuits. In some embodiments code such as software or firmware executing on at least one processing device may be used to implement one or more of the described operations or components.

The components and functions described herein may be connected and/or coupled in various ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

The signals discussed herein may take several forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A flexible implantable cardiac device configured for placement within a pericardial space, adjacent an epicardial surface having a contour, said device comprising:
a capacitor;
a battery separate from the capacitor;
an electronic component separate from both the capacitor and the battery and adapted to sense cardiac signals and to generate cardiac stimulation signals;
a plurality of flexible interconnections adapted to couple the electronic component to the capacitor and the battery;
a flexible housing having a longitudinal axis and containing the electronic component, the capacitor, the battery and the interconnections, wherein the electronic component, the capacitor and the battery are spaced apart in a linear arrangement along the longitudinal axis of the housing such that the only physical connection between the electronic component, the capacitor and the battery is provided by the interconnections, and the spacing of the electronic component, the capacitor and the battery in combination with the flexibility of the housing and the flexibility of the interconnections provides a device configured to conform to the contour of the epicardial surface; and
four electrodes carried by the flexible housing and coupled to the electronic component, wherein the spacing of the four electrodes and the flexibility of the housing are such that the device is adaptable to form an arcuate shape whereby the four electrodes form a first pair and a second pair of substantially diametrically opposite electrodes.

2. The device of claim 1 wherein the housing comprises a flexible polymer.

3. The device of claim 1 wherein the housing comprises a material having a durometer sufficient to allow the housing to conform to the contour.

4. The device of claim 1 wherein the electronic component, the capacitor and the battery are implemented with respective cross sections such that the device is adapted for implantation in the pericardial space.

5. The device of claim 1 wherein the housing comprises a flexible polymer and at least one of the electrodes comprise a portion of the polymer embedded with conductive material.

6. The device of claim 1 further comprising a plurality of pacing electrodes, coupled to the electronic component, and provided at locations on the housing such that the device is adaptable to provide pacing signals to different heart chambers via electrodes positioned adjacent to the different heart chambers.

7. The device of claim 1 wherein a first portion of the housing, including the electronic component, the capacitor and the battery, has a first cross section and a second portion of the housing, including electrodes coupled to the electronic component, has a second cross section, wherein the first cross section is wider than the second cross section.

8. The device of claim 1 comprising separate hermetic seals for the electronic component, the capacitor and the battery.

9. The device of claim 1 wherein the four electrodes are defibrillation electrodes.

10. The device of claim 1 further comprising a fixation mechanism.

11. The device of claim 1 further comprising a connector located on the housing, coupled to the battery and adapted to interface with a lead external the housing.

12. A flexible implantable cardiac device configured for placement within a pericardial space, adjacent an epicardial surface having a contour, said device comprising:
a plurality of electrodes;
a capacitor;
a battery separate from the capacitor;
a controller component separate from both the capacitor and the battery and comprising a microcontroller, a sense circuit, a pulse generator circuit and a shocking circuit, the controller component adapted to sense cardiac signals received via at least a portion of the electrodes and to generate cardiac stimulation signals output to at a least a portion of the electrodes;
a plurality of flexible interconnections adapted to couple the controller component to the electrodes, the capacitor and the battery;
a unitary, elongated and flexible housing having a longitudinal axis and at least one access hole configured to receive a guidewire, the housing containing the controller component, the capacitor, the battery and the interconnections and carrying the electrodes, wherein the controller component, the capacitor and the battery are spaced apart in a linear arrangement along the longitudinal axis of the housing such that the only physical connection between the controller component, the capacitor and the battery is provided by the interconnections, and the spacing of the controller component, the capacitor and the battery in combination with the flexibility of the housing and the flexibility of the interconnections provides a device configured to conform to the contour of the epicardial surface.

13. The device of claim 12 wherein all interconnections between the electrodes and the controller component are entirely within the housing.

14. The device of claim 12 wherein the electrodes are provided at locations on the housing such that the device is adaptable to provide pacing signals to different heart chambers via electrodes positioned adjacent to the different heart chambers.

15. The device of claim 12 wherein the plurality of electrodes comprise four electrodes, wherein the spacing of the four electrodes and the flexibility of the housing are such that the device is adaptable to form an arcuate shape whereby the four electrodes form a first pair and a second pair of substantially diametrically opposite electrodes.

* * * * *